United States Patent
Thaler et al.

[11] Patent Number: 5,602,279
[45] Date of Patent: Feb. 11, 1997

[54] PRIMARY HINDERED AMINOACIDS FOR PROMOTED ACID GAS SCRUBBING PROCESS

[75] Inventors: Warren A. Thaler, Flemington; Guido Sartori; W. S. Winston Ho, both of Annandale, all of N.J.; Larry J. Shulik, Baytown, Tex.; George E. Milliman, Fanwood, N.J.

[73] Assignee: Exxon Research and Engineering Company, Florham Park, N.J.

[21] Appl. No.: 228,535

[22] Filed: Apr. 15, 1994

Related U.S. Application Data

[63] Continuation of Ser. No. 906,779, Jun. 30, 1992, abandoned, which is a continuation of Ser. No. 546,123, Jun. 28, 1990, abandoned, which is a continuation of Ser. No. 290,126, Dec. 27, 1988, abandoned, which is a continuation-in-part of Ser. No. 179,995, Apr. 11, 1988, Pat. No. 4,919,904, which is a division of Ser. No. 93,734, Sep. 8, 1987, Pat. No. 4,759,866, which is a continuation of Ser. No. 852,322, Apr. 15, 1986, abandoned.

[51] Int. Cl.$^6$ .............................. C07C 51/295
[52] U.S. Cl. .................. 562/526; 562/553; 423/226; 423/228; 423/232; 423/243.01; 423/238; 252/189; 252/192
[58] Field of Search .................. 423/226, 228, 423/232, 238, 243.01; 252/192, 189; 562/526, 553

[56] References Cited

U.S. PATENT DOCUMENTS

| | | | |
|---|---|---|---|
| 2,384,817 | 9/1945 | Chitwood | 562/526 |
| 4,217,238 | 8/1980 | Sartori et al. | 423/226 |
| 4,759,866 | 7/1988 | Shulik et al. | 252/392 |
| 4,919,904 | 4/1990 | Shulik et al. | 423/225 |
| 5,220,055 | 6/1993 | Urano et al. | 562/539 |

OTHER PUBLICATIONS

Ullman's "Encyclopedia of Industrial Chemistry", 5th, Completely Revised Edition 1985, vol. A2, pp. 3–4.

Kirk–Othmer, "Encyclopedia of Chemical Technology," 3rd ed. (1978), vol. 1, p. 964.

The Encyclopedia Americana, International Edition (1982), vol. 1, p. 742.

McGraw–Hill Encyclopedia of Science & Technology, 7th ed. (1992), vol. 1, pp. 465–466.

Primary Examiner—Richard D. Lovering
Assistant Examiner—Valerie Fee
Attorney, Agent, or Firm—Ronald D. Hantman

[57] ABSTRACT

A gas treating composition prepared by reacting 2-amino-2-methyl-1-propanol with KOH, diluting with water and adding $K_2CO_3$ and a vanadium corrosion inhibitor.

3 Claims, 3 Drawing Sheets

PRIMARY HINDERED AMINOACIDS FOR PROMOTED ACID GAS SCRUBBING PROCESS

This is a continuation of Ser. No. 906,779, filed Jun. 30, 1992 now abandoned, which is a continuation of Ser. No. 07/546,123, filed Jun. 28, 1990, now abandoned; which a continuation of Ser. No. 07/290,126, filed Dec. 27, 1988, now abandoned; which is a CIP or Ser. No. 07/179,995, filed Apr. 11, 1988, now U.S. Pat. No. 4,919,904; which is a divisional of Ser. No. 07/093,734, filed Sep. 8, 1987, now U.S. Pat. No. 4,759,866; which is a continuation of Ser. No. 06/852,322, filed Apr. 15, 1986, now abandoned.

FIELD OF THE INVENTION

The present invention relates to the use of primary hindered aminoacids as promoters for alkali metal salts in acid gas scrubbing.

BACKGROUND OF THE INVENTION

The treatment of gaseous streams for removal of acid gases, such as hydrogen sulfide and carbon dioxide, is an essential processing step in petroleum refining, natural gas production, and the petrochemical industry. Myriad technologies have achieved commercial status, each satisfying for a particular set of circumstances a required balance among operability, process requirements, flexibility, and economic factors.

Such processes include the use of physical solvents, aqueous solutions of chemical agents (amines, carbonates, redox systems), solvent/chemical mixtures, and solid adsorbents, etc.

Historically, gas treating problems have been of three main types - hydrogen sulfide removal, the simultaneous removal of hydrogen sulfide and carbon dioxide, and carbon dioxide removal with little or no hydrogen sulfide present. The present invention pertains to the removal of acid gases, particularly to carbon dioxide, from gaseous streams containing little or no sulfur gases, such as in gaseous streams used in the manufacture of hydrogen and ammonia.

One leading type of process for the removal of $CO_2$ from gaseous streams which has met with commercial success is the so-called "hot pot" process. The hot pot process is based on the use of a hot aqueous potassium carbonate solution to convert the $CO_2$ to potassium bicarbonate. An activator, or promoter, is usually used to improve the absorption rate and/or capacity of the solution and a $V^{+5}$ salt is often used as a corrosion inhibitor. Non-limiting examples of promoters used in the hot pot process include alkanolamines, particularly diethanolamine (DEA), sterically hindered polyamines, such as N-cyclohexyl-1,3-propanediamine (CHPD) and sterically hindered amino acids such as N-secondary butyl glycine (SBG). While all of these promoters have met with varying degrees of commercial success, they are all faced with shortcomings. For example, DEA has a relatively low absorption rate and capacity and is not very stable. CHPD requires a cosolvent and undergoes degradative reactions, and SBG undergoes oxidative degradation in the presence of vanadium.

Consequently, there exists a need in the art for promoters for hot pot processes which not only have relatively high absorption rates and working capacities, but which are not susceptible to degradation under process conditions or in the presence of vanadate corrosion inhibitors.

SUMMARY OF THE INVENTION

In accordance with the present invention there is provided an aqueous gas scrubbing composition comprising:

(a) one or more alkali metal salts; and (b) the product of 2-amino-2-methyl-1-propanol (AMP) and an oxidant. In a preferred embodiment, the alkali metal salt is KOH and the product is formed in the presence of a catalyst, CdO.

Another embodiment of the present invention includes the process for making the product of 2-amino-2 methyl-1-propanol and the oxidant.

In another embodiment, the scrubbing composition also contains an effective amount of a vanadium corrosion inhibitor. That is, at least that amount which will result in the inhibition of corrosion of the metal of the process unit apparatus. Vanadium salts can be used at a concentration of about 0.001 to 10 wt. % based on vanadium metal, preferably about 0.1 to 5 wt. %, more preferably from about 0.1 to 1 wt. %.

DETAILED DESCRIPTION OF THE INVENTION

Figure 1:
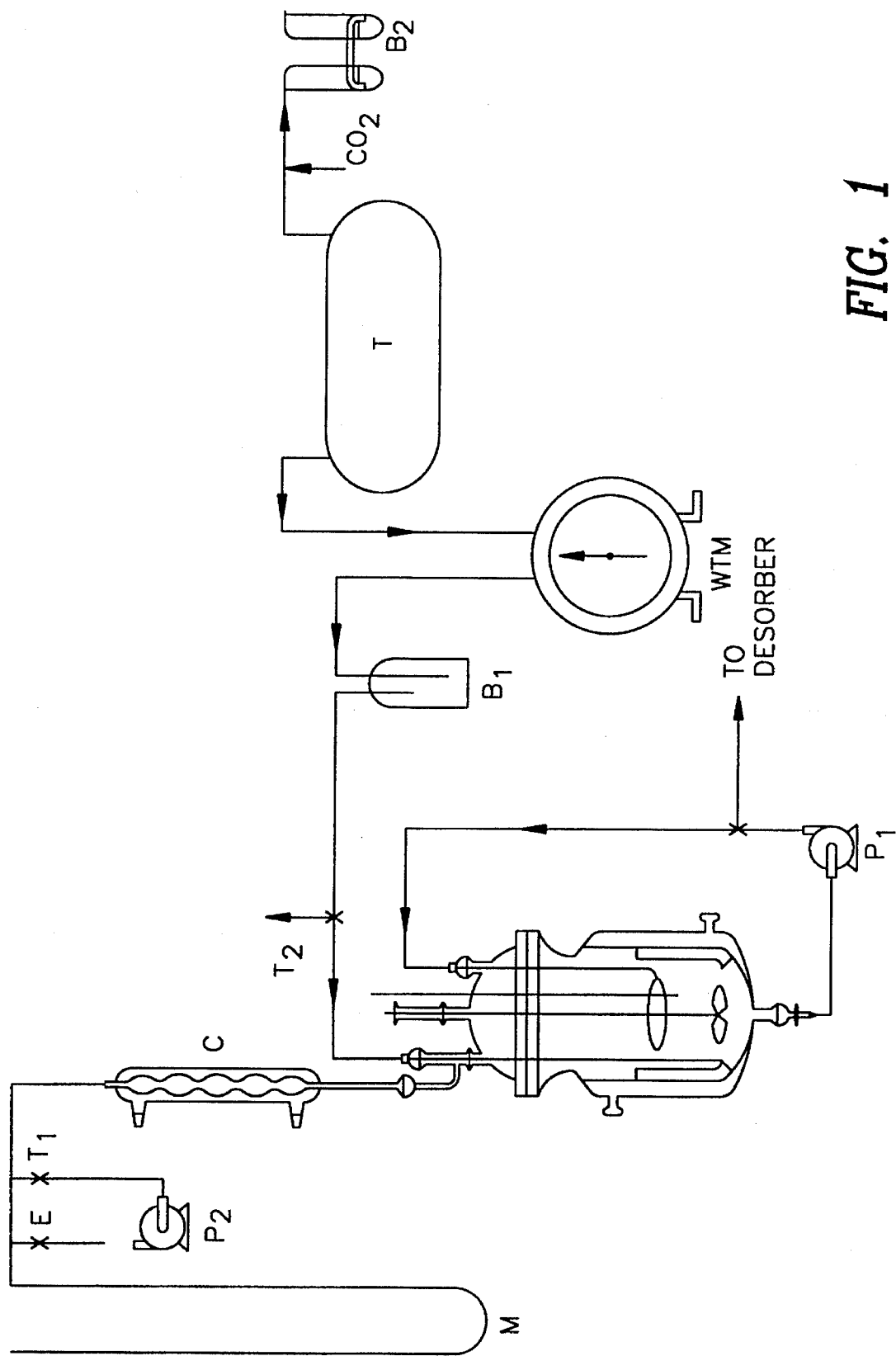
FIG. 1 shows a diagrammatic flow sheet illustrating an experimental reaction apparatus for removing carbon dioxide from gas streams.

The term, acid gas, includes $CO_2$ alone or in combination with $H_2S$, $SO_2$, $SO_3$, $CS_2$, HCN, COS and the oxides and sulfur derivatives of $C_1$ to $C_4$ hydrocarbons. These acid gases may be present in trace amounts within a gaseous mixture or in major proportions.

It is known that (see U.S. Pat. No. 4,759,866 which is incorporated herein by reference) the above acids are removed from gaseous streams by use of one or more alkali metal salts (which include hydroxides), and one or more primary sterically hindered amino acids. The primary sterically hindered amino acid can be 1-aminocyclopentane carboxylic acid or can be an amino acid represented by the formula:

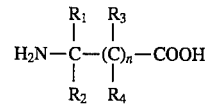

where $R_1$ and $R_2$ are independently selected from $CH_3$, $C_2H_5$, and $C_3H_7$; $R_3$ and $R_4$ are independently hydrogen and $CH_3$; and n is 0, 2, or 3. Preferably $R_1$ and $R_2$ are chosen independently from $CH_3$ and $C_2H_5$, more preferred is when both $R_1$ and $R_2$ are $CH_3$ and n is 0. It is noted that n cannot be 1 because beta amino acids in aqueous mediums undergo deamination, whereas alpha and gamma amino acids do not. A preferred composition for the amino acid is 2-aminoisobutyric acid (AIBA):

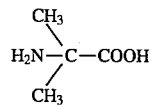

Potassium is the preferred alkali metal for use in the absorbent solutions of the present invention. Although other potassium salts of weak acids may be used, potassium carbonate, potassium hydroxide, potassium borate, and their mixtures, are preferred.

Vanadium corrosion inhibitors suitable for use herein are those vanadium compounds which contain vanadium at an oxidation state of +5 or which can undergo oxidation to result in vanadium being at an oxidation state of +5. The preferred $V^{+5}$ compound is $V_2O_5$. Preferred vanadium salts which can result in $V^{+5}$ compositions upon oxidation include the alkali metal vanadites.

The present invention is a gas treating composition for the removal of $CO_2$ by means of promoted potassium carbonate solution wherein the promoter is the oxidation product of 2 amino-2-methyl-1-propanol (AMP). The promoted gas treating composition may be derived by the insitu oxidation of AMP during the gas treating process or by the prior oxidation of AMP.

The promotor is preferably prepared from 2-amino-2-methyl-1-propanol and potassium hydroxide. The aminoalcohol is heated with an equivalent amount of solid potassium hydroxide, preferably in the presence of a catalytic quantity of a metal salt until the evolution of hydrogen ceases. A number of different metal salts worked with varying degrees of success; however, cadmium salts gave the most rapid rate of hydrogen evolution. Other metals include zinc, copper, nickel, cadmium, manganese, and cerium. Temperature range is 120°–300° C., preferably 140°–250° C., most preferably about 160°–180° C. Solid KOH (~85%) is most convenient, although aqueous solutions can be utilized, since water is removed under the reaction conditions.

An excess of KOH increases the rate of reaction. Typically a 50% excess of KOH is convenient. Under these conditions the product is a mixture of aminoisobutyric acid potassium salt and KOH. Appropriate dilution and contact with $CO_2$ converts the KOH to the carbonate-bicarbonate system so that only additional $K_2CO_3$ or $KHCO_3$ need be added. Typically, $K_2CO_3$ will comprise about 20–28% (wt) of the gas treating solution with 6–10% AIBA and about 2500 ppm $V^{+5}$ corrosion inhibitor.

The procedure described herein is an extremely convenient and economical method for the preparation of potassium AIBA solutions. The reaction proceeds in very high yield with close to the theoretical amount of hydrogen by-product evolved. Nuclear magnetic resonance analysis of the solution shows only AIBA-potassium salt. Furthermore, absorption-desorption experiments give equivalent results with comparable AIBA-$K_2CO_3$ solutions.

Our synthetic method used the AMP alcohol as received and commercial KOH (85%) in about 50% excess. The combination forms a melt under the reaction conditions. No solvent was necessary. The water present in the KOH comes off along with the hydrogen. The only product work up which we used was to dilute the final product in water and filter off the small amount of insoluble CdO catalyst.

The combination of low cost reagents which can be used without purification, the simplicity of the reaction and equipment involved with efficient use of reactor volume due to a solventless process, as well as the ability to use the product directly with essentially no work-up, makes this an attractive synthetic route to AIBA.

EXAMPLES

Example 1

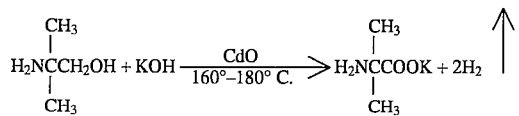

An experiment using 10 g 2-amino-2-methyl-1-propanol, 0.33 g cadmium oxide (3.3 wt. % based on amino alcohol) and 10.5 g of 85% potassium hydroxide yielded the theoretical quantity of hydrogen gas. The product was diluted with 50 ml $H_2O$ filtered and diluted to 100 ml total volume. The solution was analyzed for residual Cd which equaled 18.4 mg CdO/ml. The synthesis was repeated in a twenty-fold scale up. This time the hydrogen was measured through a wet test meter instead of a graduate cylinder. The hydrogen was measured 90% of theory. NMR analysis showed only a single product, consistent with the amino acid salt. A portion of the product was isolated as the free amino acid. Its infrared was indistinguishable from that of an authentic sample of AIBA. The solution was diluted and filtered leaving a clear solution containing 59.1% solids.

Example 2

CO$_2$ Absorption-Desorption Experiments Using Commercial AIBA

FIG. 1 shows the absorber, which is a 2-liter vessel equipped with heating mantle, thermocouple, reflux condenser, air-driven stirrer and gas inlet tube. A Pump $P_1$ can remove liquid from the bottom of the vessel and feed it back to it through sparget S.

Figure 2:
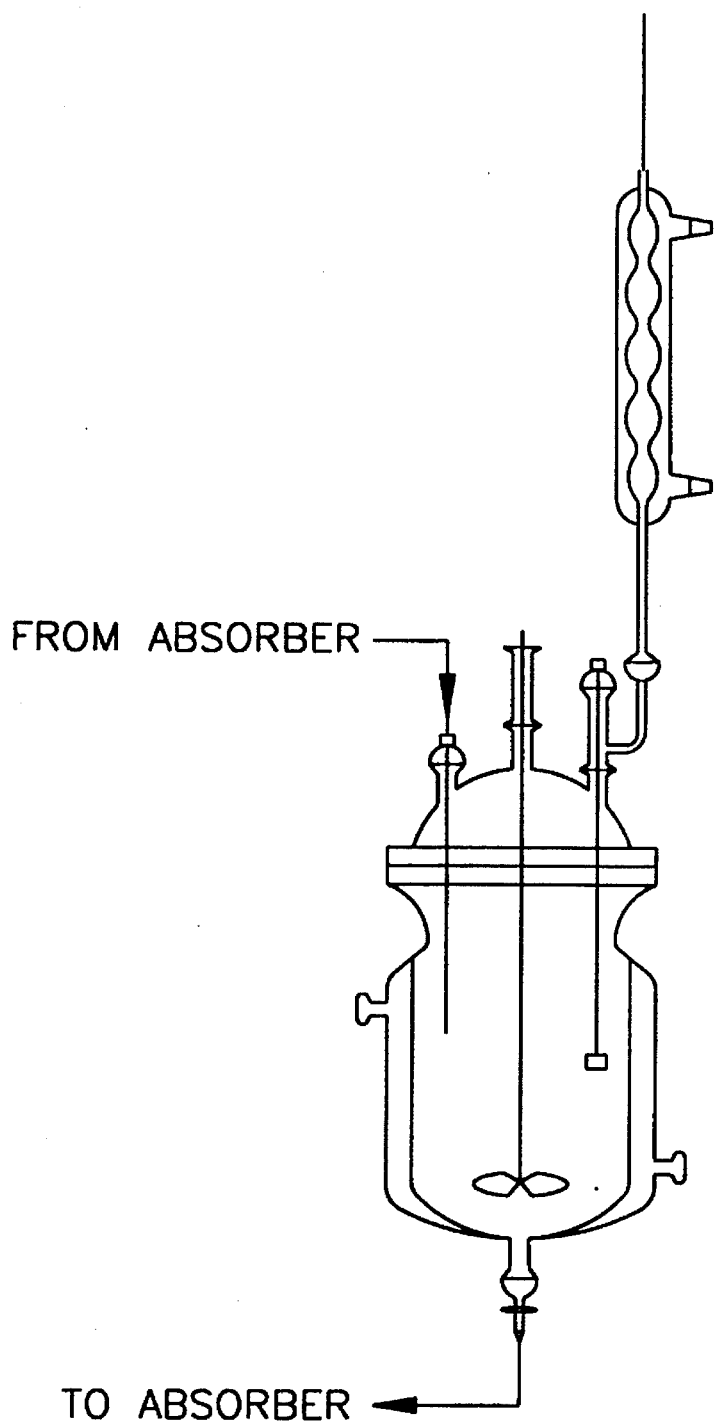
FIG. 2 shows a schematic diagram of a desorber.

FIG. 2 shows the desorber, which is a 2-liter vessel equipped with stirrer, reflux condenser, thermometer, and gas inlet tube.

The following is a detailed description of a typical experiment. The following reagents were put into a 2-liter Erlenmeyer:

75 g of 2-aminoisobutric acid (10 wt. %)
210 g of $K_2CO_3$ (28 wt. %)
465 g of $H_2O$ The flask was heated to completely dissolve the solids, then the solution was put into the absorber and brought to 83° C. while pumping it around by means of pump $P_1$; then the vessel was evacuated by means of pump $P_2$, until the solution began to boil. Valve $T_1$ was closed, the liquid circulation rate was brought to 3 liters/minute, and the stirrer was started and adjusted to 1500 rpm. Valve $T_2$ was opened, thereby admitting $CO_2$. Tank T acted as a ballast, preventing air suction through the mercury bubbler $B_2$. The 3-liter wet-test meter, WTM, indicated how many liters of $CO_2$ had been absorbed at any time. In total, 20.1 liters of $CO_2$ was absorbed. The rich solution so obtained was transferred to the desorber by means of pump $P_1$. The solution was brought to 103° C., during which time 16.5 liters of $Co_2$ was desorbed. Then the solution was refluxed for 60 minutes, during which time the temperature climbed to 105.5° C. The total amount of $CO_2$ desorbed was 31 liters.

The lean solution was then transferred back to the absorber and brought to 83° C. The same procedure was used as for the initial absorption, 30.5 liter of $CO_2$ was absorbed, of which 9.5 liters in the first minute.

Example 3

CO₂ Absorption-Desorption Using An Oxidized AMP Solution

A solution from Example 1 had the following composition: 59.1% solids; 0.493 g K-aminoisobutyrate/g solution; 0.098 g KOH/g solution.

The gas treating composition was prepared using:

208.3 g of solution (equivalent to 73.5 g 2-aminoisobutyric acid)

134.6 g of K$_2$CO$_3$ (total K equivalent to 209.7 g K$_2$CO$_3$)

407.0 g of H$_2$O

A CO$_2$ absorption-desorption experiment in the manner of Example 2 was performed using this solution. The solution reabsorbed 30.4 liter of CO$_2$, 10.5 liters in the first minute.

This result shows excellent performance for gas treating solutions prepared from the 2-amino-2-methyl-1-propanol reaction with KOH.

Example 4

Figure 3:
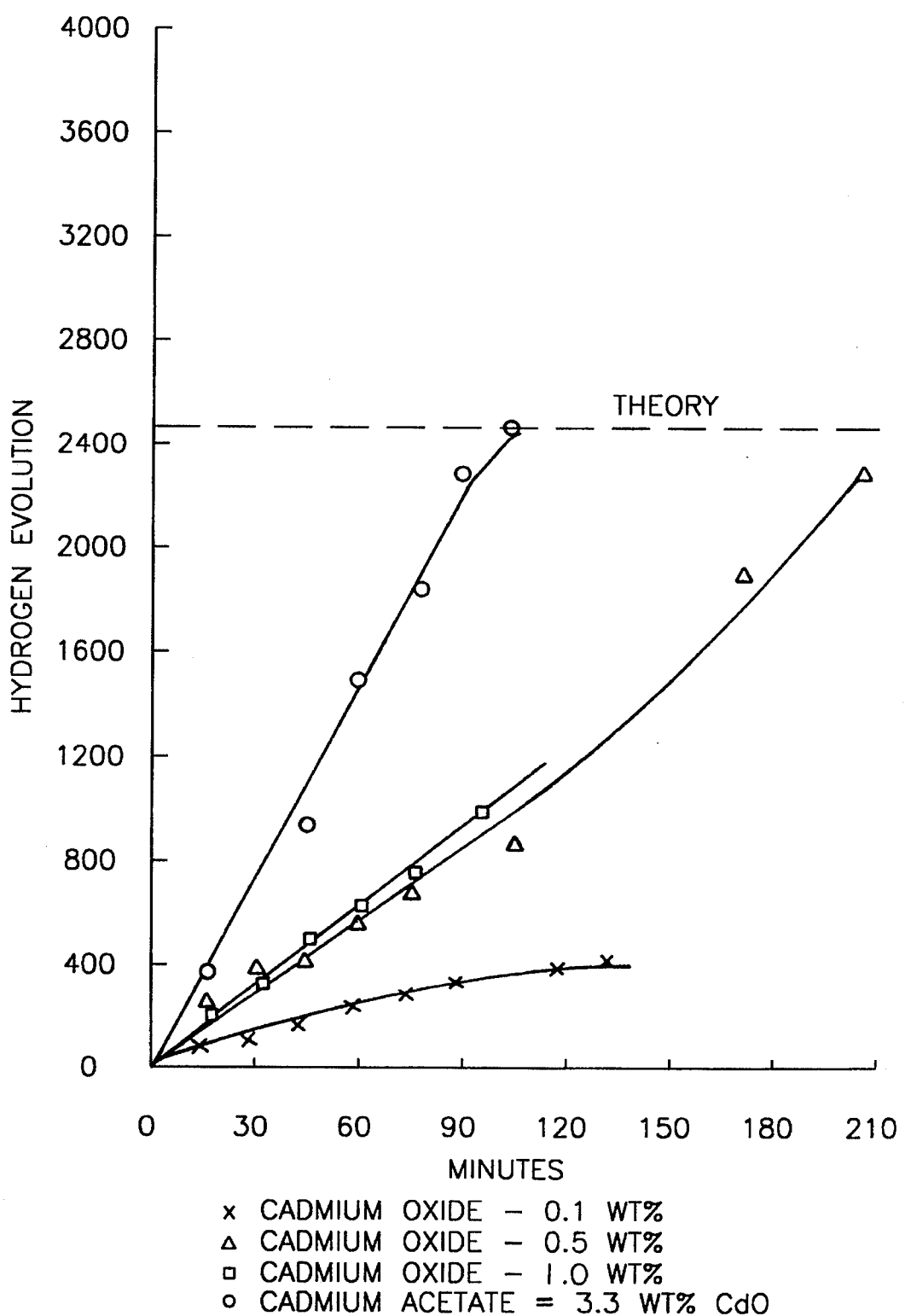
FIG. 3 shows the effect of hydrogen evolution as function of Cd concentration.

The effect of Cd concentration on the rate of hydrogen evolution was examined. The results suggest that below about 3% CdO equivalent the rate of oxidation of 2-amino-2-methyl-1-propanol is slow (FIG. 3).

What is claimed is:

1. A process for preparing a gas scrubbing solution which includes aminoisobutyric acid or its salts comprising the step of reacting the sterically hindered amine, 2-amino-2-methyl-1-propanol (AMP),

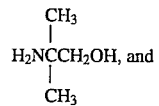

an excess of potassium hydroxide, KOH, at a temperature from about 120° C. to about 300° C. to produce said aminoisobutyric acid for said gas scrubbing solution.

2. The process of claim 1 wherein said process is carried out in the presence of a catalytically effective amount of a metal salt, wherein said metal is selected from the group consisting of Cd, Zn, Cu, Ni, V, Mn, and Ce.

3. The process of claim 2 wherein said catalyst is CdO.

* * * * *